United States Patent [19]

Pfirmann et al.

[11] Patent Number: 5,399,744
[45] Date of Patent: Mar. 21, 1995

[54] METHOD OF MANUFACTURING ISOBORNYL (METH)ACRYLATE

[75] Inventors: Martina Pfirmann, Griesheim; Joachim Knebel, Darmstedt, both of Germany

[73] Assignee: Roehm GmbH Chemische Fabrik, Darmstadt, Germany

[21] Appl. No.: 242,603

[22] Filed: May 13, 1994

[30] Foreign Application Priority Data

May 13, 1993 [DE] Germany .................. 43 16 004.2

[51] Int. Cl.$^6$ ............................................. C07C 69/02
[52] U.S. Cl. ................................................... 560/231
[58] Field of Search ................................. 560/231, 232

[56] References Cited

U.S. PATENT DOCUMENTS

| | | | |
|---|---|---|---|
| 3,088,969 | 5/1963 | Callahan et al. | 260/486 |
| 4,103,032 | 7/1978 | Farooq | 514/719 |
| 4,521,634 | 6/1985 | Fujioka et al. | 568/665 |
| 4,715,981 | 12/1987 | Fujioka et al. | 252/174.11 |

FOREIGN PATENT DOCUMENTS 1954986 6/1970 Germany .
3034033 11/1970 Germany .

OTHER PUBLICATIONS

Derwent Abstracts, AN-83-42349K, JP-A 58 049 337, Mar. 23, 1983.
Chemical Abstracts, vol. 92, 1980, AN-92:60517h, JP-A-79 126 293, Oct. 1, 1979.

*Primary Examiner*—Arthur C. Prescott
*Attorney, Agent, or Firm*—Oblon, Spivak, McClelland, Maier & Neustadt

[57] ABSTRACT

The subject invention pertains to a method of manufacturing isobornyl acrylate or isobornyl methacrylate by reacting camphene with acrylic acid or methacrylic acid, respectively, in the presence of a molybdenum heteropolyacid as a catalyst.

17 Claims, No Drawings

METHOD OF MANUFACTURING ISOBORNYL (METH)ACRYLATE

BACKGROUND OF THE INVENTION

1. Field of the Invention

The present invention pertains to a method of manufacturing acrylic acid esters and methacrylic acid esters by catalytic addition of the corresponding acid to an alkene. The invention particularly pertains to a method of manufacturing isobornyl acrylate and isobornyl methacrylate.

2. Description of the Related Art

Carboxylic acids can be added to olefins under acid catalysis, to equilibrium conversion. This method represents a supplement to the customary transesterification or esterification reactions; with olefin addition one can produce esters of secondary and particularly tertiary alcohols, which otherwise are difficult to produce. Catalysts used may be proton acids or Lewis acids such as boron trifluoride (see Houben-Weyl, 1952, Vol. 8, p. 534). The higher the degree of substitution (by alkyl substituents) at the double bond and the more acidic the carboxylic acid, the more favorable is the equilibrium to the side of the ester.

Examples which might be cited are the production of acetates or formates from isobutene, isopentene, dicyclopentadiene, norbornene, or camphene. The production of isobornyl acrylate from camphene and acrylic acid, with $H_2SO_4$ as catalyst, is described in Japanese Pat. 79-126293 (ref.: CA 92:60,517).

Acid ion exchangers have also been used as catalysts for the reaction. Thus, the production of isobornyl (meth)acrylate from camphene and (meth)acrylic acid using a strongly acid ion exchanger is described in Japanese Pat. 58-049337. However, in this process, long reaction times (>8 hr) are needed to reach equilibrium conversion. This results in poor space-time yields, with a detrimental effect on manufacturing costs. Also, operating over such long reaction times at high temperatures necessitates stabilization of the reaction mixture (to avoid polymerization), and may additionally present more serious problems.

German laid-open application DE 19 54 986 claims heteropolyacids of molybdenum or tungsten as catalysts to produce organic compounds by reacting olefins with carboxylic acids (including unsaturated carboxylic acids) to form the corresponding esters. According to German laid-open application DE 30 34 033, dihydrodicyclopentyl acrylate (or methacrylate) can be produced by reacting dicyclopentadiene, an endocyclic diolefin, with acrylic acid or methacrylic acid respectively, in the presence of a tungsten heteropolyacid compound as catalyst. The present applicants were unable to successfully employ tungsten heteropolyacid catalysis in the reaction of camphene with (meth)acrylic acid, however.

Industry has been deterred in the greater use of the interesting compounds isobornyl acrylate and isobornyl methacrylate, particularly as comonomers in the production of industrially and commercially useful polymers, due to insufficiencies in the known manufacturing methods for the subject compounds.

Industrial use of the known methods is difficult due to factors such as long reaction times as in the above-mentioned acid ion exchange catalysis; corrosion effects of mineral acids and boron trifluoride on process equipment; and the need to neutralize such soluble catalysts and remove them from the product by water washing and/or extraction of the reaction mixture, all of which make the refining of the product quite complex. Moreover, catalysts such as many Lewis acids present problems with respect to environmentally acceptable disposal. Purification by distillation of the product in the presence of the catalyst is not possible because unreacted carboxylic acid (which is volatile) will be distilled off, which will shift the reaction equilibrium away from formation of the ester.

OBJECTS OF THE INVENTION

For production of isobornyl acrylate and isobornyl methacrylate from camphene and the corresponding unsaturated acids, a catalyst is needed which has high activity and therefore provides a short reaction time, and which can be separated easily from the product after the reaction, thereby enabling purification of the product by distillation.

It has now been surprisingly discovered that of a number of tested heteropolyacids, only poly-phosphomolybdic acid, particularly $H_3PMo_{12}O_{40} \cdot xH_2O$, shows the necessary activation, i.e. acceleration of the reaction of camphene with (meth) acrylic acid or acrylic acid to produce the corresponding isobornyl ester. With other heteropolyacids, e.g. vanadium analogs of phosphomolybdic acid, the amount of ester formation detected was small to none.

It was surprising and unforeseeable that the reaction of dicyclopentadiene with (meth)acrylic acid described in German laid-open application DE 30 34 033 is not catalyzed by the same phosphomolybdic acid which is highly effective in the inventive method, and that (as mentioned above) the corresponding phosphotungstic acid does not show any catalytic activity in the formation of isobornyl (meth)acrylate.

SUMMARY OF THE INVENTION

Accordingly, the present invention pertains to a method of manufacturing isobornyl acrylate or isobornyl methacrylate by reacting camphene with acrylic acid or methacrylic acid, respectively, in the presence of a polyphosphomolybdic acid catalyst.

Advantageously the heteropolyacid catalyst is removed by filtration following the reaction, preferably following addition of alkali to cause any dissolved catalyst to precipitate, more preferably after dilution with an organic solvent. The alkali, which may be, for example NaOH, KOH, NaHCO$_3$ or NaOCH$_3$, is preferably added as an aqueous or methanolic solution after the reaction, in amounts approximately equivalent to the amount of heteropolyacid employed. The recovered heteropolyacid may optionally be reused for the reaction of camphene with one of the unsaturated acids. It is also possible to carry out the reaction in an organic solvent.

DESCRIPTION OF THE PREFERRED EMBODIMENTS

The amount of catalyst used for the reaction is preferably 0.1–5 wt.%, more preferably 0.1–3 wt.%, based on the total weight of the reaction partners employed. Advantageously camphene is used in a molar ratio of 0.5:1 to 2:1, particularly 0.8:1 to 1.2:1, with respect to the unsaturated acid employed. The reaction temperature is preferably in the range of 40°–140° C., more preferably 60°–100° C. At temperatures appreciably above 100° C. polymerization may occur, particularly of the unsaturated acid or the reaction product; at temperatures below 40° C. the reaction rate is very low. Reaction times in the range 1–5 hr are preferred.

Normally the reaction is carried out in a closed system, in which a suitable pressure is established for the given reaction temperature. However, the reaction may be conducted at substantially elevated pressure, or reduced pressure.

Preparation of isobornyl (meth)acrylate by the process of the invention may be conducted batchwise or continuously. Because the starting substances and the reaction products can polymerize, polymerization inhibitors, e.g. hydroquinone, phenothiazine, hydroquinone methyl ether, etc. are generally added both during the reaction and in the refining steps. Following the reaction, the catalyst is substantially removed to produce an essentially catalyst free crude product mixture. By the term "essentially catalyst free" is meant that the phosphomolybdic acid catalyst is removed to the extent that distillation of the crude product mixture may be accomplished without significant loss of product as described heretofore. Suitable alkali materials which may assist in complete removal of catalyst are, for example, the alkali metal hydroxides, bicarbonates, carbonates, and alkoxides.

Having generally described this invention, a further understanding can be obtained by reference to certain specific examples which are provided herein for purposes of illustration only and are not intended to be limiting unless otherwise specified.

Examples 1

Production of isobornyl methacrylate

In a solution of 204.4 g (1.5 mol) camphene in 140 mL methacrylic acid (1.65 mol, stabilized with 60 mg hydroquinone and 30 mg phenothiazine), 3.46 g phosphomolybdic acid was suspended. The mixture was stirred 3 hr at 80° C. while bubbling air through the mixture. After cooling to room temperature, 1.5 g concentrated potassium hydroxide was added to the mixture, and the mixture was filtered to remove the catalyst. After distillation, 178 g isobornyl methacrylate was obtained (53% of theoretical, b.p. 74°–80° C. at c.a. 0.4 mbar).

Production of isobornyl acrylate

In a solution of 1.36 kg (10 mol) camphene in 0.76 L acrylic acid (11 mol, stabilized with 0.4 g hydroquinone and 0.2 g phenothiazine), 21.6 g phosphomolybdic acid was suspended. The mixture was stirred 3 hr at 80° C. while bubbling of air through the mixture. After cooling to room temperature, 9 g concentrated potassium hydroxide was added to the mixture, and the mixture was filtered to remove the catalyst. After distillation 1050 g isobornyl acrylate was obtained (50% of theoretical).

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for the manufacture of isobornyl acrylate or isobornyl methacrylate comprising reacting camphene with acrylic acid or methacrylic acid respectively, in the presence of a catalyst comprising a polyphosphomolybdic acid.

2. A process according to claim 1, wherein the polyphosphomolybdic acid is $H_3PMo_{12}O_{40} \cdot xH_2O$.

3. A method according to claim 1 wherein alkali is added after the reaction, and precipitated phosphomolybdic acid is filtered out.

4. A method according to claim 2 wherein alkali is added after the reaction, and precipitated phosphomolybdic acid is filtered out.

5. A process according to claim 1 wherein an organic solvent is added during the reaction and/or during removal of the catalyst.

6. A process according to claim 2 wherein an organic solvent is added during the reaction and/or during removal of the catalyst.

7. A process according to claim 3 wherein an organic solvent is added during the reaction and/or during removal of the catalyst.

8. A process according to claim 4 wherein an organic solvent is added during the reaction and/or during removal of the catalyst.

9. A process for the manufacture of isobornyl (meth)acrylate, comprising the steps of:
   (a) reacting camphene with (meth)acrylic acid in the presence of phosphomolybdic acid;
   (b) removing phosphomolybdic acid from the reaction mixture obtained from (a) to form a crude product mixture;
   (c) distilling the crude product mixture (b) to obtain a purified isobornyl (meth)acrylate product.

10. The process of claim 9 wherein said reacting step (a) is performed in the presence of an organic solvent.

11. The process of claim 9 wherein the reaction step (a) is performed over a temperature range of from about 40° C. to about 100° C.

12. The process of claim 9 wherein removal of catalyst from the reaction mixture is assisted by the addition of alkali to the reaction mixture (a) in an amount effective to precipitate the catalyst.

13. The process of claim 12 wherein said alkali is selected from the group consisting of the alkali metal hydroxides, alkali metal bicarbonates, alkali metal carbonates, and alkali metal alkoxides.

14. The process of claim 13 wherein said alkali metal is sodium or potassium.

15. The process of claim 1 wherein air is passed through the reaction mixture.

16. The process of claim 2 wherein air is passed through the reaction mixture.

17. The process of claim 9 wherein during the reacting step (a) air is passed through the reaction mixture.

* * * * *

UNITED STATES PATENT AND TRADEMARK OFFICE
CERTIFICATE OF CORRECTION

PATENT NO. : 5,399,744
DATED : March 21, 1995
INVENTOR(S) : Martina PFIRMANN, et al.

It is certified that error appears in the above-indentified patent and that said Letters Patent is hereby corrected as shown below:

On the title page, Item [75], the second inventor's city of residence should read:

--Darmstadt--

Signed and Sealed this

Thirtieth Day of May, 1995

Attest:

BRUCE LEHMAN

Attesting Officer  Commissioner of Patents and Trademarks